United States Patent [19]

La Haye et al.

[11] Patent Number: 5,156,852
[45] Date of Patent: Oct. 20, 1992

[54] COMPOSITION AND METHOD FOR COMBATING MACULAR DEGENERATION

[75] Inventors: Peter G. La Haye, Medina, Wash.; Randall J. Olson, Salt Lake City, Utah

[73] Assignee: La Haye Laboratories, Inc., Redmond, Wash.

[21] Appl. No.: 761,694

[22] Filed: Sep. 18, 1991

Related U.S. Application Data

[63] Continuation-in-part of Ser. No. 341,025, Apr. 20, 1989, Pat. No. 5,075,116.

[51] Int. Cl.5 .................. A61K 33/24; A61K 33/34; A61K 33/32; A61K 31/525
[52] U.S. Cl. ..................... 424/617; 424/630; 424/639; 424/641; 424/702; 514/251; 514/345; 514/458; 514/474; 514/494; 514/562; 514/912
[58] Field of Search ............. 424/630, 617, 641, 639, 424/702; 514/251, 345, 458, 474, 562, 912, 494

[56] References Cited

U.S. PATENT DOCUMENTS 4,002,758  1/1977  Bigóu ..................... 514/912
5,075,116 12/1991  La Haye et al. ......... 424/617

OTHER PUBLICATIONS

Machlin, Lawrence J., et al., FASEB J., 1: 441–445 (1987) "Free Radical Tissue Damage: Protective Role of Antioxidant Nutrients".

Primary Examiner—Frederick E. Waddell
Assistant Examiner—Raymond J. Henley, III
Attorney, Agent, or Firm—Gordon W. Hueschen

[57] ABSTRACT

In accordance with the present invention, a composition is provided with Vitamins C and E, zinc acetate, copper, selenium, manganese, and at least one of L-cysteine, pyridoxine, and riboflavin. The Vitamins C and E serve as antioxidants, while the zinc acetate, copper, selenium and manganese serve as cofactors for metalloenzymes which scavenge oxidizers. The remaining three compounds tend to enhance glutathione concentration. All the elements are provided in a tablet or caplet form which is suitable for oral ingestion. Preferably, the composition is taken periodically each day of a treatment period.

12 Claims, No Drawings

COMPOSITION AND METHOD FOR COMBATING MACULAR DEGENERATION

This application is a continuation-in-part of our prior-filed copending application Ser. No. 07/341,025, filed Apr. 20, 1989, now U.S. Pat. No. 5,075,116.

BACKGROUND OF THE INVENTION

1. Field of the Invention

The present invention generally relates to a method and composition for the alleviation of eye diseases and, more specifically, to an improved method and composition for combating macular degeneration.

2. Description of the Related Art

Macular degeneration associated with aging and drusen is an extremely significant concern, and is now a major cause of blindness in the United States for individuals over 65 years of age. Just at the period of time when the eyes are a most important sense, and reading and watching television are often the most enjoyable avenues of entertainment, this disease robs the elderly patient of such possibilities.

The crystalline lens of the eye has only one disease state that we are aware of, and that is cataract. The lens loses its clarity as it becomes opacified, and vision is disturbed depending on the degree of opacification. There are different etiologies for cataracts such as a congenital lesion or trauma, which are well recognized. It is also known that some medicines such as cortisone-type preparations and glaucoma medications can cause cataracts, as can inborn metabolic errors such as galactosemia. These, however, are relatively uncommon in comparison to the common aging cataract, which shows an increase in frequency directly correlated with age.

The exact incidence of cataracts in the general population is difficult to determine because it depends on one's definition of a cataract. If defined as simply a lens opacity, then obviously the incidence is much higher than when defined as a lens opacity that significantly impacts vision. The pathogenesis of age-related cataracts and macular degeneration is incompletely understood.

Macular degeneration associated with aging and drusen also appears to be a biodegeneration with no effective treatment to date except with laser treatment in patients who develop abnormal vessels under the retina, i.e., subretinal neovascularization. The treatable group is a distinct minority of a much larger group. That means that individuals so afflicted can anticipate either a progressive deterioration or at times relatively static course, but no spontaneous improvement, since the basic architecture of the retina is destroyed. Occasionally, there may be variations in vision which seem to show improvement depending on such things as lighting in the room and potential resolution of fluid underneath the retina. The important point, however, is that when this sensitive neurologic tissue is damaged, that damage is permanent.

In 1981, Spector et al. stated that there still remained questions concerning the mechanism and agents involved with massive oxidation of the lens tissue and its relationship to cataract development. Spector, Exp. Eye Res., 33:673, 1981. They also noted that glutathione (GSH) can act as a reducing agent and free radical trapper. GSHPx and catalase are present to metabolize $H_2O_2$. SOD can detoxify $O_2$, and light can photochemically induce oxidation. However, Spector et al. believed that the actual roles of light and/or metabolically-generated oxidized components are unclear as to causing the observed oxidation products.

In 1987, Machlin et al. reported that there was some evidence that free radical damage contributed to the etiology of some diseases, including cataract. FASEB J. 1:441-45, 1987. They indicated that defenses against such free radical damage included Vitamin E, Vitamin C, betacarotene, zinc, iron, copper, manganese, and selenium.

As recently as 1988, in an article by Jacques et al., "Antioxidant Status in Persons With and Without Senile Cataract," Arch. Ophthal. 106:337, 1988, it is reiterated that it is commonly believed that oxidative mechanisms are causally linked to, not simply associated with, cataract formation. According to Jacques et al., the evidence suggests that GSHPx and SOD decrease with increasing degree of cataract.

Jacques et al. further reported that Vitamin E is believed to be a determinant of cataract formation and can act synergistically with GSHPx to prevent oxidative damage. They point out the possibility that Vitamin C may have a role in cataract formation and might influence GSHPx through its ability to regenerate Vitamin E.

If a treatment modality could slow down the progression of cataracts or macular degeneration, it would have a tremendous impact on the number of individuals who suffer from these problems due to the fact that they both occur toward the end of life. Toxicity from free radicals and oxidizers has generated significant interest in both diseases. There is circumstantial evidence at present to indicate that protection against phototoxicity and oxidizers could slow the onset and progression of both ailments.

While the problems associated with cataracts and macular degeneration have long been recognized, and many attempts have been made to identify the causative factors and to solve such problems, those diseases still remain as major health problems.

A need therefore still exists in the art to provide improved methods and compositions for the treatment of macular degeneration in the absence of a surgical solution.

SUMMARY OF THE INVENTION

Accordingly, an object of the present invention is to provide a treatment methodology for eye diseases.

Another object of the present invention is to provide a safe yet effective composition for combating macular degeneration.

Still another object of the present invention is to provide a composition for scavenging free radicals and other oxidants associated with eye diseases.

In accordance with the present invention, a composition is provided with Vitamins C and E, zinc acetate, copper, selenium, manganese, and at least one of L-cysteine, pyridoxine, and riboflavin. The Vitamins C and E serve as antioxidants, while the zinc, copper, selenium and manganese serve as cofactors for metalloenzymes which scavenge oxidizers. The remaining three compounds tend to enhance glutathione concentration. All the elements are preferably provided in a caplet form which is suitable for oral ingestion. Preferably, the composition is taken periodically each day of a treatment period.

The above and additional objects of the present invention can best be seen from an examination of the following specification and claims.

DETAILED DESCRIPTION OF THE PREFERRED EMBODIMENTS

The following description is provided to enable any person skilled in the art to which the present invention pertains, or with which it is most nearly connected, to make and use the same, and sets forth the best mode contemplated by the inventors of carrying out their invention.

According to the present invention, the elements of the composition are directed to scavenge free radicals and oxidants or in other ways retard disease progression of macular degeneration. The free radicals to which the present invention is directed primarily include superoxide. The oxidants primarily include peroxide.

The items and doses in the present invention are consistent with those readily available in health food stores. The composition is preferably in tablet or caplet form for oral administration, with the patient taking two to four tablets or caplets twice a day. The present inventions, however, contemplates that the preferred total dosage can be administered as a single dose or other multiple part dosages. The composition may also be of the timed release type. Further, for oral administration, the present composition may be in capsules, lacquered tablets, or unlacquered tablets, according to well-known methods. In accordance with the preferred multiple dosages described above, each tablet or caplet is preferably composed approximately as follows:

Vitamin C

It has been known that there are high concentrations of Vitamin C both in the normal human lens and in the aqueous humor that surrounds the lens, and that this is an antioxidant. Harris, Nature 132:27-8, 1933, It has also been shown in the past that generally increasing dietary Vitamin C generally increases the concentration of ascorbate in the aqueous humor and in the human lens. Ringvold, Acta, Ophthalmologica 63:227-80, 1985. It has also been known that Vitamin C concentrations decrease with age and, in particular, in patients who have senile cataract. Chatterjee, Arch, Ophthalmol 56:756-60, 1956; Purcell, Arch, Ophthalmol 51:1-6, 1954; Consul, Eye, Ear, Nose and Throat Monthly 47:77, 1968. However, the latter study concluded that a fall in the level of ascorbic acid is not related to the causation of cataract. Purcell, supra. concluded that the therapeutic administration of Vitamin C to patients with cataracts appears irrational.

There is no known optimal daily dose of Vitamin.C, although the U.S. RDA is 60 mg. However, dosages of 2.0 grams and more have frequently been taken as a supplement for general health. Although ascorbic acid or rose hips can be used, the present composition preferably utilizes Vitamin C in the form of sodium ascorbate because of it being easily dissolved in the digestive system and causing relatively minimal irritation. The concentration is at about 200-250 mg/tablet or caplet, or a preferred total dosage of about 0.8-2 grams/day. In such concentrations, the Vitamin C represents about 20-30% by weight of each tablet or caplet, which includes active as well as inactive ingredients described below.

Vitamin E

Vitamin E is also a well-known antioxidant, as already mentioned. See also Mansour, Invest. Opthal. Vis. Sci. (Supp) 25:138, 1984. As also mentioned above, Vitamin E can work synergistically with Vitamin C in protecting vital cell function from normal oxidants. Orten: *Human Biochemistry* 10th Edition, CV Mosby Co., 1982, p. 756.

A very common Vitamin E supplementation consists of 400 units per day. While one study which used 800 units per day showed questionable signs of toxicity, many common dietary supplements available in supermarkets have 1000 units of Vitamin E daily. Chaney: *Textbook of Biochemistry with Clinical correlations,* John Wiley & Sons, 1986, pp. 970-1. The U.S. RDA is 300 units. The present invention preferably uses Vitamin E in the form of d-alpha tocopherol because of the ease of dissolving and minimal irritation. The preferred concentration is at about 60-75 units/tablet or caplet or a total daily dosage of 240-400 units of Vitamin E, or even higher. This represents about 6-9% by weight of each tablet or caplet.

Zinc

Zinc is known to be important to the health of the retina and the function of Vitamin A. Russel, Ann Int Med 99 227-39, 1983; Karcioglu, Surv Ophthalmol 27:114-22, 1982; Leure-duPree, Retina 2:294-302, 1982; Leure-duPree, Invest Ophthalmol Vis Sci 23:425-34, 1982. Zinc is one supplement previously used in a study which showed it to be significantly better than placebo in retarding macular degeneration changes. Newsome, Arch Ophthalmol 106:192-8, 1988. Zinc is also known to be an important cofactor for a whole multitude of metalloenzymes, not the least of which is superoxide dismutase, which scavenges the potent oxidizer - superoxide. There are two types of SOD in mammalian cells. One type contains copper and zinc and is located in the cytosol and periplasmic space of the mitochondria. The other type contains manganese and is in the matrix of the mitochondria (see generally U.S. Pat. No. 4,657,928). This is of particular import because both superoxide dismutase activity and zinc are dramatically lower in cataract patients than in noncataract patients. Ohrloff, Graefe's Arch Clin Exp Ophthalmol 222:79-81, 1984; Varma, Ophthalmic Res 9:421-31, 1977; Swanson, Biochem Biophy Res Comm 45:1488-96, 1971.

About 200 mg of zinc per day, although well-tolerated, has been shown to have potential side effects, particularly blocking copper absorption, which results in the possibility of copper deficiency anemia. Fischer, J Nutrition 113:462-9, 1983. High doses have also been shown to have the effect of lowering high density lipoprotein which may exacerbate atherosclerosis. Hooper, JAMA 244:1960-1, 1980.

The dosages of 100 mg of zinc a day and 150 mg of zinc a day have been known in the past to be well tolerated without difficulty. Wagner, Geriatrics 40:111-25, 1985. The U.S. RDA is 15 mg. While other salt forms such as sulfate, picolinate, phosphate, and gluconate can be used, the present invention preferably provides the zinc in the form of zinc acetate, because of it being most readily dissolved, causing minimal irritation, and effecting most rapid, complete (highest amount), and greatest percentage conversion into plasma zinc content, all of which are most desirable aspects. The concentration is preferably at about 20–30 mg of zinc as the zinc acetate in each tablet or caplet for a total dosage of approximately 80–150 mg/day. Zinc (in the form of acetate) most preferably represents about 1.0–2.5% by weight of each tablet or caplet.

Copper

Copper is another important cofactor for metalloenzymes, and is a second necessary cofactor for superoxide dismutase. Beem, J Biol Chem 249:7298, 1974. Copper has been shown to decrease in individuals over 70 years of age and to be basically zero in cataractous lenses. Swanson, Biochem Biophy Res Comm 45:1488–96, 1971. If copper is significantly decreased, superoxide dismutase has been shown to have decreased function, thereby hampering an important protective lens mechanism. Williams, Pediat Res 1:823, 1977. Copper is also protective of zinc toxicity, which blocks some of the zinc absorption and, therefore, decreases bioavailability. Van Campen, J Nutrition 97:104–8, 1970.

2–3 mg of copper per day has been estimated to be safe and provide adequate daily dietary intake. Pennington, J Am Dietetic Assoc 86:876–91, 1986. 2 mg is the U.S. RDA. Some copper absorption will be blocked by the 100 mg of daily zinc as provided above. Van Campen, J Nutrition 7:104–8, 1970. Therefore, the present composition preferably utilizes about 1–1.5 mg/tablet or caplet, or a total of about 4–6 mg/day. This amount is considered safe because in the typical American diet, particularly among the elderly, zinc and copper are often significantly below minimum daily requirements. In this embodiment of the present invention, copper is provided in the form of copper gluconate or an amino acid chelate and copper in such form preferably represents about 0.1–0.2% by weight of each tablet or caplet.

Selenium

Selenium is another metal which has been known to be markedly deficient in cataracts versus clear lenses. Swanson, Biochem Biophy Res Comm 45:1488–96, 1971. Selenium is a necessary cofactor for metalloenzymes, particularly GSHPx, which scavenges peroxides. Chaney, at p. 988. A past study showed macular degeneration being inversely related with plasma activity of GSHPx and suggested that its activity is an indication of the adequacy of selenium nutritional status. Weiter, Invest Ophthalmol (Supp) 26:58, 1985. Other studies have documented that selenium deficiency results in markedly decreased activity of lens GSHPx in animals, and the addition of selenium in selenium deficient animals blocked cataract formation. Whanger, Nutr Rep Int 12:343, 1975; Lawrence, Exp Eye Res 18:563, 1974.

The presently-accepted safe and adequate daily dietary intake of selenium is about 50 to 200 micrograms (mcg) for an adult. There is no U.S. RDA for selenium. Typical dietary intake for adults is in the lower end of the above range. A presently accepted, estimated safe daily selenium human intake is 5 micrograms per kilogram of body weight per day. In the present composition, selenium is added at about 20–30 mcg/tablet or caplet, or a total of 80–120 mcg/day. Selenium, which is preferably bound with a primary dried yeast or in the form of selenomethionine, preferably represents at least about 1.0 and preferably up to about 2.5% by weight of each tablet or caplet.

Manganese

In general, manganese concentration has been known to decrease in cataracts versus clear lenses, although not nearly as dramatically as copper, zinc and selenium. Swanson, Biochem Biophy Res Comm 45:1488–96, 1971. Manganese is an important cofactor for metalloenzymes. Orten, at pp. 725–6. As briefly noted above, a second type of superoxide dismutase exists in the mitochondria and has manganese as a necessary cofactor. Another metalloenzyme, to which manganese is a cofactor, is methionine adenosyl-transferase, which is found in the lens. See generally Geller, Exp. Eye. Res. 43:998, 1986.

There is no presently known minimum daily requirement of manganese. However, a daily dose of 10 mg is an accepted safe amount and commonly available in the supermarket. Preferably, manganese is provided in the present composition at about 5 mg/tablet or caplet, or a total of 20 mg/day. This preferably represents about 0.1–0.5% by weight, while preferably being provided in the form of manganese gluconate or an amino acid chelate.

L-Cysteine

Glutathione (GSH), a tripeptide which includes L-cysteine, has been called the Achilles' heel of the human lens system. Cole, JAMA 254:1008, 1985. It, as alluded to above, acts directly as an antioxidant intracellularly and is also an important constituent of many enzymes, not the least of which is GSHPx, which reduces the potent oxidizer–peroxide. Reddy, Exp Eye Res 11:310–28, 1971; Bhuyan, Biochem Biophys Acta 497:641–51, 1977; Kinoshita, Am J Ophthalmol 46:36–41, 1958; Pirie, Biochem J 96:244–53, 1965. Glutathione has been known to decrease in concentration in human cataracts. Consul, Eye, Ear, Nose and Throat Monthly 47:77–80, 1968. Of the three constituent amino acids, L-cysteine is the one which has been thought to be rate limiting in regard to glutathione synthesis. Rathbun, In: Hockwin O (Ed.) *Altern der Linse.* Wilhelm Mayr, 1982, pp. 169–74.

L-cysteine is a naturally occurring amino acid. A total dose of 400 mg per day of L-cysteine is readily available to someone on a high protein diet. The present composition uses L-cysteine, when present, at about 50 mg/tablet or caplet, or a total of about 400 mg/day. L-cysteine bound with hydrogen chloride is naturally occurring and, when present, preferably represents about 7.353% by weight of each tablet or caplet.

Pyridoxine

Pyridoxine, or water soluble Vitamin $B_6$, is known to be important for protein synthesis in general and may enhance glutathione production. Chaney, at pp. 976–8. The U.S. RDA for Vitamin $B_6$ is 2 mg/day. Due to the known importance of glutathione in maintaining lens clarity, pyridoxine, when present, is preferably added to the present composition in a dose of about 6.25 mg/tablet or caplet, or about 50 mg/day. This is about 0.742% by weight of each tablet or caplet. Although the dose is much greater than the minimum daily requirement, it is apparently safe and is not an uncommon dose in multivitamins available in drugstores or grocery stores.

Riboflavin

Riboflavin, or water-soluble Vitamin $B_2$, has previously shown a good correlation with riboflavin nutritional status in older patients between those who had clear lenses and those who had cataracts. Skalka, Metabolic Ped Ophthalmol 5:17-20, 1981; Bhat, Nutr Rep Int 36:685, 1987. Glutathione reductase is necessary to reduce glutathione after oxidation, and riboflavin deficiency is associated with decreased glutathione reductase activity. Srivastava, Exp Eye Res 16:519, 1973. This enzyme is lower in cataractous lenses and would appear to be necessary if the glutathione system is to operate as an antioxidant. Beutler, Science 165:613-5, 1969; Day, Am J Ophthalmol 14:1005-9, 1931; Ono, Internat J Vit Nutr Res 46:422-6, 1976; Yagi, 10th International Congress of Nutrition, Abstract No. 3211, p. 169 (August 1975).

40 mg a day is a common dosage of riboflavin and is available in supermarkets. The U.S. RDA is about 1.7 mg. Preferably, about 10 mg/tablet or caplet is used in the present composition, or a total of 40-60 mg/day, which represents at least about 1% by weight.

The present composition may also include bioflavonoid (Vitamin P) or betacarotene (Vitamin A) as an addition to and/or substitute for one or more of the active ingredients.

The combination of vitamins, including glutathione-enchancing vitamins, is preferably present in an aggregate amount of at least about 30% by weight of the composition.

As noted above, inactive elements which are well known in the art, are preferably provided as fillers to put the active elements in tablet or caplet form. For example, the fillers may include binders, lubricants, and disintegrants, which could include cellulose, gelatin, and silica.

The above active elements, considered separately, have been known to provide certain physiological effects, as described above. However, many of the studies have been animal-oriented, in vitro and it has not been apparently known that the above combination can provide synergistic benefits. As a partial consequence thereof, whether in caplet form or otherwise, the above daily dosages can change to either a greater or smaller quantity, depending upon the severity of the disease and the patient's individual circumstances. In other words, four caplets may be sufficient for one patient, while another patient may require six caplets. Eight caplets, as described above, should remain the maximum, unless special circumstances dictate otherwise. Accordingly, any treatment period can change, which is dependent upon the daily dosage. In many instances, since the objective is to prevent or slow the disease, the treatment period will be indefinite.

The above only describes preferred embodiments of the present invention, and it is contemplated that various modifications to the above can be effected but nevertheless come within the scope of the following claims.

We claim:

1. A method for combating macular degeneration, consisting essentially of the step of concurrently orally administering to a patient in need thereof
   an effective amount of a plurality of antioxidants for minimizing oxidative reactions;
   an effective amount of a plurality of cofactors for activating metalloenzymes which react with said metallo-enzymes to increase the effectiveness thereof for scavenging oxidants; and
   an effective amount of one or more glutathione-elevating compounds for elevating glutathione production and/or concentration;
   said antioxidants including at least Vitamin C and Vitamin E;
   said cofactors being selected from the group consisting of zinc, copper, selenium, and manganese;
   and said glutathione-elevating compounds being selected from the group consisting of L-cysteine or a salt thereof, pyridoxine, and riboflavin.

2. The method according to claim 1 wherein said cofactors include all of copper, selenium, manganese, and zinc acetate.

3. The method according to claim 1 wherein said glutathione-elevating compounds include at least riboflavin.

4. The method according to claim 1 comprising oral administration of said composition taken on a periodic basis each day over the course of a treatment period.

5. The method of claim 1, wherein zinc is present in the form of zinc acetate.

6. A method for combating macular degeneration, comprising the step of orally administering to a patient in need thereof a composition consisting essentially of:
   an effective antioxidant amount of a plurality of vitamins including at least Vitamins C and E;
   an effective amount of a plurality of cofactors for metalloenzymes selected from the group consisting of zinc, copper, selenium, and manganese, for the activation of metalloenzymes for the scavenging of oxidants; and
   an effective amount of at least one enhancer of glutathione production and/or concentration selected from the group consisting of L-cysteine or a salt thereof, pyridoxine, and riboflavin.

7. The method according to claim 6 wherein said vitamins including glutathione-enhancing vitamins are present in an aggregate amount of at least about 30% by weight of said composition.

8. The method according to claim 6 wherein said cofactors are present in the form of a salt or in bound form in an aggregate amount of at least about 2% by weight of said composition.

9. The method according to claim 6 wherein said composition is in an orally ingestible tablet or caplet form.

10. The method according to claim 6 wherein at least riboflavin is included as a glutathione-enhancer.

11. The method of claim 6 for combating macular degeneration, wherein said composition consists essentially of
   vitamin C in an amount of at least about 20% by weight;
   vitamin E in an amount of at least about 6% by weight;
   zinc in the form of zinc acetate in an amount of at least about 1.0% by weight;
   copper in a pharmaceutically-acceptable ingestible form in an amount of at least about 0.1% by weight;
   selenium in an amount of at least about 1.0% by weight;
   manganese in a pharmaceutically-acceptable ingestible form in an amount of at least about 0.1% by weight; and
   riboflavin in an amount of at least about 1.0% by weight;
   all weight percentages being percentages by weight of the total composition.

12. The method of claim 6, wherein zinc is present in the form of zinc acetate.

* * * * *

UNITED STATES PATENT AND TRADEMARK OFFICE
CERTIFICATE OF CORRECTION

PATENT NO. : 5,156,852

DATED      : Oct. 20, 1992

INVENTOR(S) : Peter G. La Haye, Randall J. Olson

It is certified that error appears in the above-identified patent and that said Letters Patent is hereby corrected as shown below:

Column 3, line 24/25; "inventions," should read -- invention, --.

Column 5, line 17; "1:823," should read -- 11:823,--.

Column 5, line 27; "7:104-8," should read -- 97:104-8, --.

Signed and Sealed this

Eighteenth Day of January, 1994

Attest:

BRUCE LEHMAN

Attesting Officer    Commissioner of Patents and Trademarks